United States Patent
Bernhard et al.

(10) Patent No.: US 10,029,024 B2
(45) Date of Patent: Jul. 24, 2018

(54) HANDPIECE FOR TREATING WOUNDS

(71) Applicant: MEDAXIS AG, Baar (CH)

(72) Inventors: Jérôme Bernhard, Zürich (CH); Lukas Christen, Lucerne (CH); Albora De Pablo Peña, Zürich (CH); Kuno Limacher, Steinhausen (CH); Martin Schug, Meggen (CH); Maryline Simon, Unterägeri (CH); Beat Widmer, Lucerne (CH); Roland Wiget, Küssnacht am Rigi (CH)

(73) Assignee: MEDAXIS AG, Baar (CH)

( * ) Notice: Subject to any disclaimer, the term of this patent is extended or adjusted under 35 U.S.C. 154(b) by 34 days.

(21) Appl. No.: 14/912,559

(22) PCT Filed: Sep. 4, 2014

(86) PCT No.: PCT/EP2014/068848
§ 371 (c)(1),
(2) Date: Feb. 17, 2016

(87) PCT Pub. No.: WO2015/032863
PCT Pub. Date: Mar. 12, 2015

(65) Prior Publication Data
US 2016/0199595 A1 Jul. 14, 2016

(30) Foreign Application Priority Data

Sep. 6, 2013 (EP) .................................... 13183380

(51) Int. Cl.
*A61M 35/00* (2006.01)
*A61L 2/00* (2006.01)
(Continued)

(52) U.S. Cl.
CPC ........ *A61L 2/0047* (2013.01); *A61B 17/3203* (2013.01); *A61B 90/30* (2016.02);
(Continued)

(58) Field of Classification Search
CPC .............. A61L 2/0047; A61B 17/3203; A61M 3/0279; B24C 5/02; A61C 1/088; A61C 17/0202; A61C 17/02
See application file for complete search history.

(56) References Cited

U.S. PATENT DOCUMENTS

2003/0153961 A1* 8/2003 Babaev ................ A61B 18/203
607/89
2009/0162810 A1* 6/2009 Werner .................. A61C 17/20
433/119
(Continued)

FOREIGN PATENT DOCUMENTS

EP 2251142 A1 11/2010
WO WO-97/02058 A1 1/1997
(Continued)

OTHER PUBLICATIONS

International Search Report for International Application No. PCT/EP2014/068848, dated Oct. 16, 2014.
(Continued)

*Primary Examiner* — Ariana Zimbouski
(74) *Attorney, Agent, or Firm* — Marshall, Gerstein & Borun LLP (57) ABSTRACT

A system for treating, in particular cleansing, wounds with a fluid jet. The system includes a handpiece with a main body with a front end with an emergence opening for the emergence of the fluid jet. The system furthermore has at least one light-emitting light source, which irradiates aerosols created when cleansing the wound. The system enables wound cleansing with simultaneous decontamination of the aerosols created in the process such that the risk of contamination of the surroundings is reduced and preferably with simultaneously treating the wound with UV light.

2 Claims, 9 Drawing Sheets

(51) Int. Cl.
  *A61B 17/3203* (2006.01)
  *B24C 5/02* (2006.01)
  *A61M 3/02* (2006.01)
  *A61B 90/30* (2016.01)
  *A61N 5/06* (2006.01)

(52) U.S. Cl.
  CPC ............ *A61M 3/0279* (2013.01); *B24C 5/02* (2013.01); *A61B 2090/309* (2016.02); *A61N 2005/0661* (2013.01)

(56) References Cited

U.S. PATENT DOCUMENTS

| | | | | |
|---|---|---|---|---|
| 2009/0204188 | A1* | 8/2009 | Perez | A61B 5/0084 607/92 |
| 2009/0227998 | A1* | 9/2009 | Aljuri | A61B 17/32037 606/13 |
| 2009/0276952 | A1* | 11/2009 | Wooten | A61H 33/6063 4/541.6 |
| 2009/0326489 | A1 | 12/2009 | Kensy et al. | |
| 2012/0045730 | A1* | 2/2012 | Sayder | A61C 17/02 433/29 |
| 2013/0122449 | A1* | 5/2013 | Weathers, Jr. | A61C 17/0202 433/25 |
| 2013/0270445 | A1 | 10/2013 | Gaska et al. | |
| 2014/0194850 | A1* | 7/2014 | Vinchon | A61M 5/344 604/506 |

FOREIGN PATENT DOCUMENTS

| | | |
|---|---|---|
| WO | WO-2006/097133 A1 | 9/2006 |
| WO | WO-2006/107343 A2 | 10/2006 |
| WO | WO-2008/074284 A2 | 6/2008 |
| WO | WO-2010/123627 A2 | 10/2010 |

OTHER PUBLICATIONS

English Translation of International Preliminary Report on Patentability for International Application No. PCT/EP2014/068848, dated Mar. 17, 2016.

* cited by examiner

HANDPIECE FOR TREATING WOUNDS

CROSS-REFERENCE TO RELATED APPLICATION

The present application is the US national phase of International Patent Application No. PCT/EP2014/068848, filed Sep. 4, 2014, which application claims priority to Europe Application No. 13183380.8, filed Sep. 6, 2013. The priority application, EP 13183380.8, is hereby incorporated by reference.

TECHNICAL FIELD

Field of the Disclosure

The present invention relates to a handpiece and a method for treating, in particular cleansing, wounds with a fluid jet.

Prior Art

Wound cleansing/debridement and wound rinsing/wound toilet refers to the medical procedure for removing infected, damaged or dead (necrotic) tissue from ulcers, burns and other wounds or in the case of organ decay. There are numerous general approaches for cleansing wounds, e.g. mechanical sharp approaches using a scalpel or a sharp spoon, enzymatic or chemical, or autolytic, biosurgical, mechanical approaches using pads and a fluid jet.

EP 2 251 142 shows a handpiece for cleansing wounds with a high-pressure micro-fluid jet, wherein an emergence opening is arranged at the front end of the handpiece, through which a fluid jet can emerge.

WO 97/02058 discloses a handpiece for cleansing wounds by means of a water jet, wherein the water used for cleansing is sterilized in advance by means of UV irradiation.

WO 2010/123627 discloses a combined device with a UV-A or UV-C light source, an optical identification unit and a fluid supply and suctioning unit. All three units are connected to a common cable which, at the free end thereof, has three mutually separated outlets for image identification, UV light irradiation and fluid supply and suctioning. Here, the UV light irradiation is used for therapeutic purposes.

In the case of cleansing wounds by means of fluid jet, coatings or particles are removed from the wound, with aerosols being created in the process. It is important to ensure that the surroundings are not contaminated by these aerosols since this constitutes a danger to the patient or the operating staff. The prior art has disclosed various methods of reducing or preventing the contamination of the surroundings by the aerosols. Such methods, such as e.g. returning of the liquid, a shielding treatment tent with an exhaust lock or the arrangement of the fluid jet and the suction unit in a covering hood, are mentioned in WO 2008/074284.

The use of a system with an covering hood is only possible to restricted extent, depending on the type, size and location of the wound to be cleansed. If the hood is too small, only small wounds can be treated therewith or the hood must be placed onto part of the wound, which may be painful for the patient and disadvantageous for wound healing. However, if the hood is too large, the sealing-off in relation to the surrounding tissue is difficult. If a treatment tent is used, this does simplify the sealing-off, but such tents are unwieldy as they have little inherent stability and they reduce the view of the wound to be cleansed.

DISCLOSURE OF THE INVENTION

It is therefore an object of the present invention to reduce the risk of contamination of the surroundings during the treatment, in particular the cleansing, of a wound.

The system according to the invention for treating, in particular cleansing, wounds with a fluid jet comprises a handpiece, which has a main body with a front end with an emergence opening for the emergence of the fluid jet. The system furthermore has at least one light-emitting light source, which irradiates aerosols created when cleansing the wound. The at least one light source is arranged in such a way that the light emitted by the at least one light source surrounds the fluid jet that emerged from the emergence opening at least at one distance from the emergence opening. The at least one light source is arranged in such a way in relation to the emergence opening that the emerged fluid jet is approximately completely surrounded by the emitted light.

The light source is a light-emitting element. In one embodiment, the light is generated in the light source itself. In another embodiment, the light source is an emergence opening of an optical waveguide. Surface areas which have a sufficiently lustrous embodiment to reflect incident light but are not part of an optical waveguide are not understood to be light sources, neither within the meaning of this text and nor in the art.

The at least one light source can be arranged separately from the handpiece. However preferably it is arranged in or at the handpiece such that the handpiece itself forms the system.

The fluid jet can emerge from one or more emergence openings.

Preferably, the fluid jet is a micro-fluid jet, in particular a high-pressure micro-fluid jet. In this case, in particular, the pressure range from 100 to 300 bar is understood to mean high pressure. However, it is also conceivable for the fluid jet to be generated with a pressure of less than 100 bar. The fluid is usually an aqueous solution or a treatment solution, such as e.g. a sterile saline. The fluid jet preferably has a diameter of approximately 0.05 mm to 0.15 mm when emerging from the emergence opening.

The light, in particular the UV light, can be used during the wound cleansing by the fluid for the purposes of minimizing viable germs in the treatment space and, preferably, also in the wound itself. Aerosols created during the wound cleansing can be irradiated and decontaminated immediately in situ, and during the cleansing of the wound and this can take place before they are able to contaminate the surroundings. The effect is increased if the light surrounds the fluid jet, particularly in the region of the incidence thereof on the wound. Preferably, the light surrounds the fluid jet completely, at least in this region.

Wound healing can be promoted by irradiating the wound during the cleansing. Moreover, the UV irradiation can constitute an alternative to antimicrobial salves and antibiotics.

A further advantage is that, particularly in the case of relatively small wounds, there no longer is a need for tents, hoods or suction devices, and so viewing the wound is possible without restrictions. Moreover, the treatment time and the treatment costs are reduced by simplifying the employed means.

The UV light (ultraviolet light) preferably has a UV-C light component (100-280 nm). In a preferred embodiment, it is only, or at least predominantly, UV-C light that is present.

Additionally or alternatively, the UV light has a UV-A or a UV-B light component or consists exclusively of UV-A or UV-B.

Preferably, the UV light is coherent light, preferably laser light.

Preferably, the light source is a UV-C light source in the range of 200 to 280 nm. In this range, the light has an increased germicidal effect. A particularly effective region of the wavelength lies at approximately 260 nanometer. Therefore, use is preferably made of light sources with a wavelength of 254 nanometers.

Preferably, the light of the light source is generable in the handpiece. This is advantageous in that the intensity of the radiation is not attenuated by e.g. optical waveguides. However, it is also conceivable to generate the light in a rear region of the handpiece and to use short optical waveguides in order to guide the light substantially in the jet/beam direction.

The light source is preferably arranged in a region of the front end in the vicinity of where the fluid jet emerges. For light sources with the same strength, the following applies: the closer the light source is to the region to be irradiated, the higher the energy density is in the irradiated region and the more effective the irradiation is.

The light power of the light source can be fixed or regulable. The electric feed of the light source can be carried out by a light-source line or electric line, which connects an external current source with a handpiece, or it can be carried out by electric stores, e.g. batteries or accumulators, provided in the handpiece.

Preferably, downstream, the fluid jet extends, adjacent to the emergence opening, at least partly within the emitted light. Preferably, it extends within the light up to the incidence thereof on the wound. The closer the light source is guided to the wound, the more effective the irradiation of the aerosols is.

Preferably, the at least one light source is arranged at or in the front end of the handpiece in a manner surrounding the emergence opening. However, it can also be arranged in an adapter or at the holder, which is arrangeable at the handpiece. This arrangement at the handpiece can be detachable or fixed.

The at least one light source preferably has a diameter that is many times greater than the cross section of the fluid jet. The closer the at least one light source is arranged to the fluid jet and the larger the light source is in comparison with the diameter of the fluid jet, the smaller the shadow caused by the fluid jet is. A small shadow region is advantageous in respect of irradiating the aerosols created by the wound cleansing or in respect of the wound surface.

Ideal irradiation of the aerosols or the wound surface can be achieved by the number, the arrangement, the embodiment of the light sources and the selection of possible beam directing and/or expanding optics.

The handpiece can taper at the front end in order not to impede the irradiation where possible, or it can expand in order to be able to receive larger light sources.

The handpiece preferably has a front end surface, on which the emergence opening of the fluid jet is arranged, wherein the at least one light source, in respect of the front end face, is arranged recessed therefrom, flush therewith or protruding therefrom in the emergence direction of the fluid jet. Depending on the application, it is advantageous for the light sources to be as small as possible, i.e. so that they do not impede the view of the user where possible, or for these to be as large as possible, i.e. so that they generate a high radiation intensity. The type and size of the light sources require corresponding recesses in the handpiece or in the adapter part. Depending on the required size of the light source and the required view of the wound to be cleansed, it is advantageous to have a different arrangement of the light sources in respect of the front end face.

Preferably, the front end of the handpiece has a recess for receiving the light source. Therefore, the light sources are well integrated into the handpiece and at least partly protected from external influences.

The recess preferably expands in the emergence direction of the fluid jet. As a result of the expansion of the recess, the light is not impeded by the handpiece and a light cone irradiating a region representing a multiple of the area of the cross section of the fluid jet can be formed. Preferably, the recess expands in all directions so that a light cone that is as large as possible can be formed.

Use can be made of larger light sources if the front end of the handpiece expands in the emergence direction of the fluid jet. The expansion can be uniform at the circumference. However, it can also be realized only in the regions with the light sources. As a result, it is possible to achieve a compromise between a simple construction and a good visibility of the wound for the user.

One, two, three, four, five, six or more light sources may be present. The radiation intensity can be influenced by the number, the arrangement and the regulation of the power of the light sources.

Preferably, the at least one light source has a light-emergence region which has a round, oval, quadratic, rectangular, polygonal or toroidal embodiment. By using commercially available light sources, the costs for custom products can be saved.

Preferably, the emergence opening is arranged centrally in the front end. As result of the central arrangement, the handpiece can have a substantially rotationally symmetric embodiment, leading to simplified handling for the user since the manner in which the handpiece is held is unimportant.

The light source is preferably a light-emitting diode (LED), an LED arranged on a printed circuit board (PCB) or an LED integrated into an integrated circuit board (ICB). Light-emitting diodes are distinguished by a long service life and lack of sensitivity in relation to tremors. They convert the employed energy more effectively into light than other light sources and produce less heat in the process and only require a low operating voltage.

In one embodiment of the invention, the front end has an optical waveguide which distributes light emitted by the light source substantially in the direction of the fluid jet. By using an optical waveguide, the light generated by the light source can be directed in a specific manner. The form of the light source then has less influence on the formation of the respective light cone. Likewise, it is possible to irradiate specific regions more intensely than other regions. It is thus also possible to irradiate regions which cannot be irradiated in a direct manner.

Preferably, the front end has a nozzle, which forms the emergence opening or is flush therewith. Preferably, the light source is arranged adjacent to the nozzle. The nozzle determines the quality and the form of the fluid jet. Arranging the light sources adjacent to the nozzle optimizes the ability of irradiating the aerosols by the light sources thanks to the vicinity to the fluid jet.

Preferably, the handpiece has a rigid embodiment.

Further embodiments are specified in the dependent claims.

BRIEF DESCRIPTION OF THE DRAWINGS

Preferred embodiments of the invention are described below on the basis of the drawings, which merely serve for explanatory purposes and should not be construed as being restrictive. In the drawings:

DESCRIPTION OF PREFERRED EMBODIMENTS

Figures 1, 2:
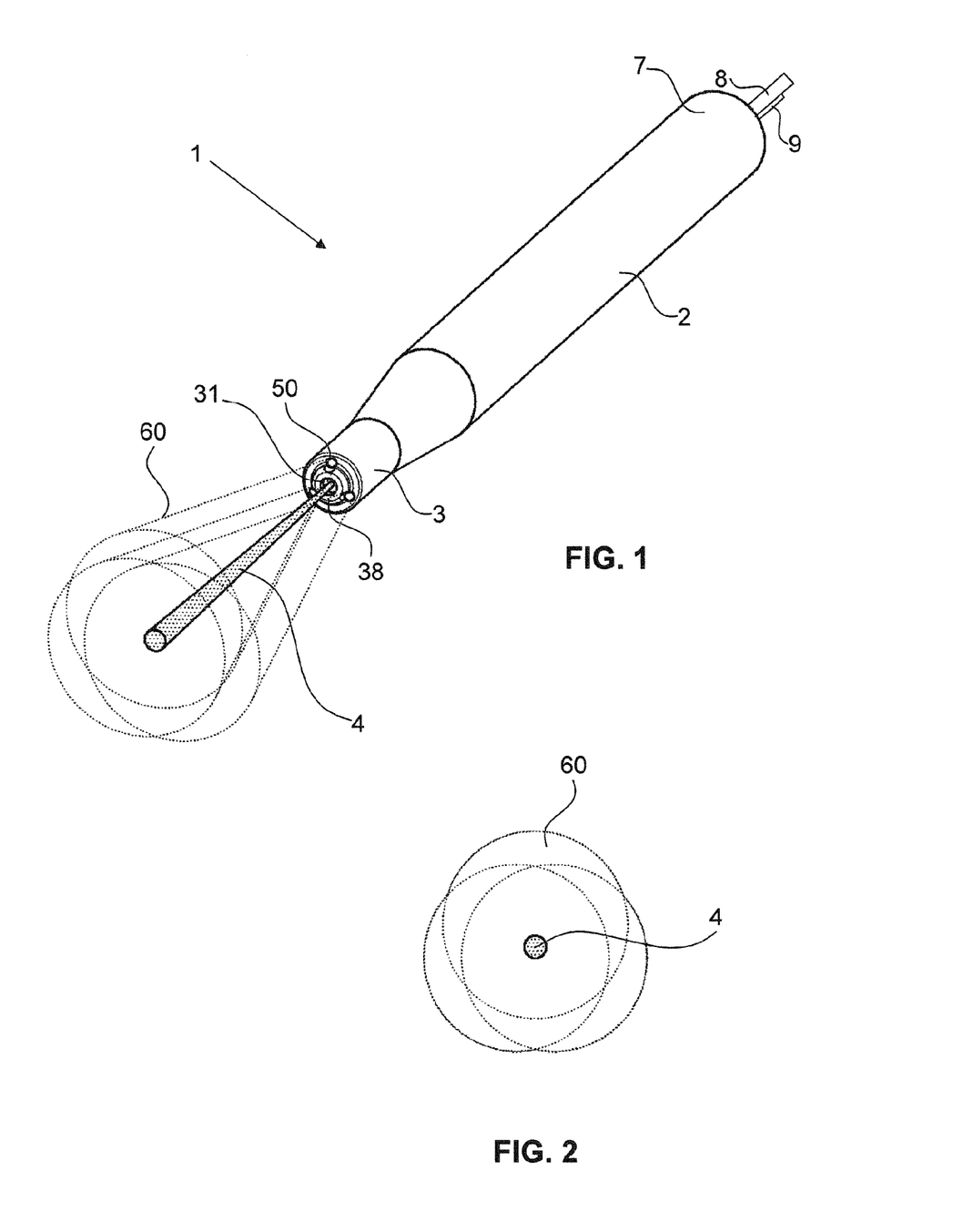
FIG. 1 shows a perspective illustration of the first embodiment of a system according to the invention for cleansing wounds with a fluid jet, with a light cone and fluid jet.
FIG. 2 shows an illustration of an area with a fluid jet illuminated by a handpiece in accordance with FIG. 1.
Figure 4:
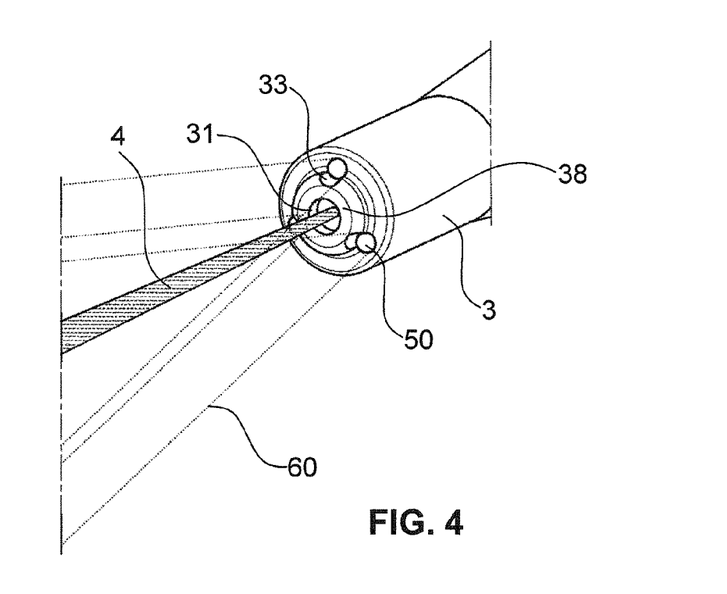
FIG. 4 shows a magnified perspective illustration of a front end of a handpiece in accordance with FIG. 1, with a light cone and fluid jet.

FIG. 1 shows a perspective illustration of a first embodiment of a system according to the invention for treating, in particular for cleansing, wounds with a fluid jet, with first light cones 60 and a fluid jet 4, wherein the system is a handpiece 1 in this embodiment. FIG. 4 shows a perspective illustration of a front end 3 of the handpiece 1. The handpiece 1 has a substantially cylindrical main body 2 with the front end 3 and a rear end 7. The front end 3 has an emergence opening 31 for the emergence of the fluid jet 4. The emergence opening 31 is arranged centrally in a front end face 38 of the handpiece 1. The handpiece 1 is embodied in such a way that the fluid jet 4 emerges from the emergence opening 31 in a manner substantially collinear in relation to the central axis of the main body 2. Three first light sources 50 are preferably arranged at the front end 3. The first light sources 50 are distributed uniformly over the circumference of the front end 3 around the emergence opening 31. The first light sources 50 are embodied in such a way that a region, which is in front of the handpiece 1 in the jet/beam direction, can be irradiated. Preferably, the region of the fluid jet 4, surrounded during use and adjacent thereto, can be irradiated completely such that, where possible, all created aerosols are captured by the light beam.

FIG. 2 shows an illustration of an area with a fluid jet 4 illuminated by the handpiece 1 in accordance with FIG. 1. This corresponds to a radiation cross section through the fluid jet 4 and the first light cones 60, downstream of the emergence opening 31, during use. Although the ratios change with the distance from the emergence opening 31, the fluid jet 4 remains arranged substantially in a center of overlapping regions of the first light cones 60. First recesses 33 for receiving the first light sources 50 form light-emergence regions, which have a substantially round embodiment in this embodiment. Therefore, the first light cones 60 irradiate a substantially circular area. Together with FIG. 1, it is possible to identify that the first light cones 60 completely envelop the fluid jet 4.

FIG. 1 furthermore shows that the rear end 7 has a fluid line 8 and an electric line 9, wherein the fluid line 8 ensures the supply of the handpiece 1 with a fluid, preferably an aqueous solution or treatment solution, such as e.g. a sterile saline, and the electric line 9 ensures at least the power supply for the light sources 50. The subsequent embodiments of the handpiece 1 according to the invention likewise have a pressure line 8 and an electric line 9 at the rear end 7, but these are not depicted in these figures.

Figure 3:
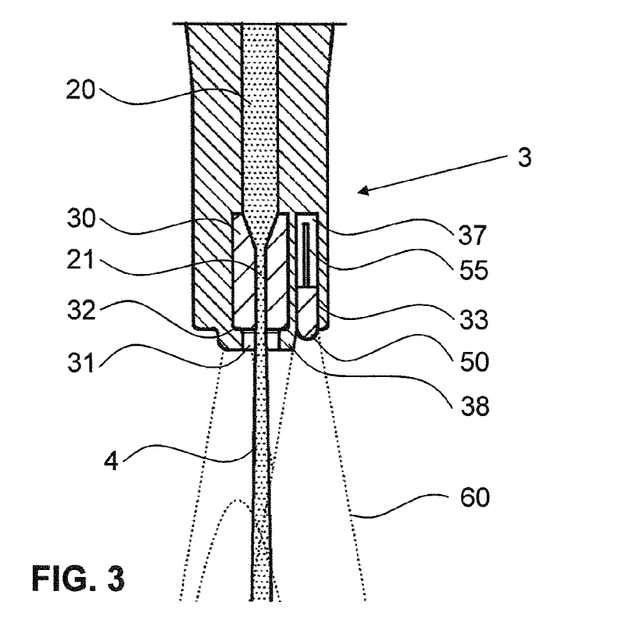
FIG. 3 shows a central sectional view of a front end of a handpiece in accordance with FIG. 1, with a light cone and fluid jet.

FIG. 3 shows a central sectional view of the front end 3 of the handpiece 1 in accordance with FIG. 1, with light cones 60 and fluid jet 4. The front end 3 comprises a centrally arranged fluid channel 20, a nozzle 30 flush therewith, which nozzle in turn is flush with the emergence opening 31, and first recesses 33 radially distributed at the circumference around the emergence opening 31 for receiving the first light sources 50.

The substantially cylindrical nozzle 30 is received in a known manner in the front end 3 of the handpiece 1 and the position thereof in the jetbeam direction is determined by a front stop 32. The nozzle 30 has a nozzle channel 21 arranged centrally therein. The configuration of this channel determines the emergence geometry of the fluid jet 4.

The first light sources 50 are preferably UV-C light-emitting diodes with round cross sections.

Fifth recesses 37 for the electrical supply of the first light sources 50, so called light-source lines 55 are provided adjoining the first recesses 33 for the first light sources 50. Preferably, the light-source lines 55 are brought together at the rear end 7 and guided in a common electric line 9 to a supply unit (not depicted here). The subsequent embodiments of the handpiece 1 according to the invention likewise have fifth recesses 37 for receiving the light-source lines 55.

The first light sources 50 are arranged recessed in relation to the front end face 38. In order not to impede the light from the first light sources 50 where possible, the first recesses 33 have a conical embodiment in the front regions thereof. What is achieved thereby is that the fluid jet 4 is surrounded by light from the first light source 50 as soon as possible after the emergence from the emergence opening 31. Therefore, the aerosols created in the process are also irradiated in the case of short treatment distances from the wound.

Figures 5, 6:
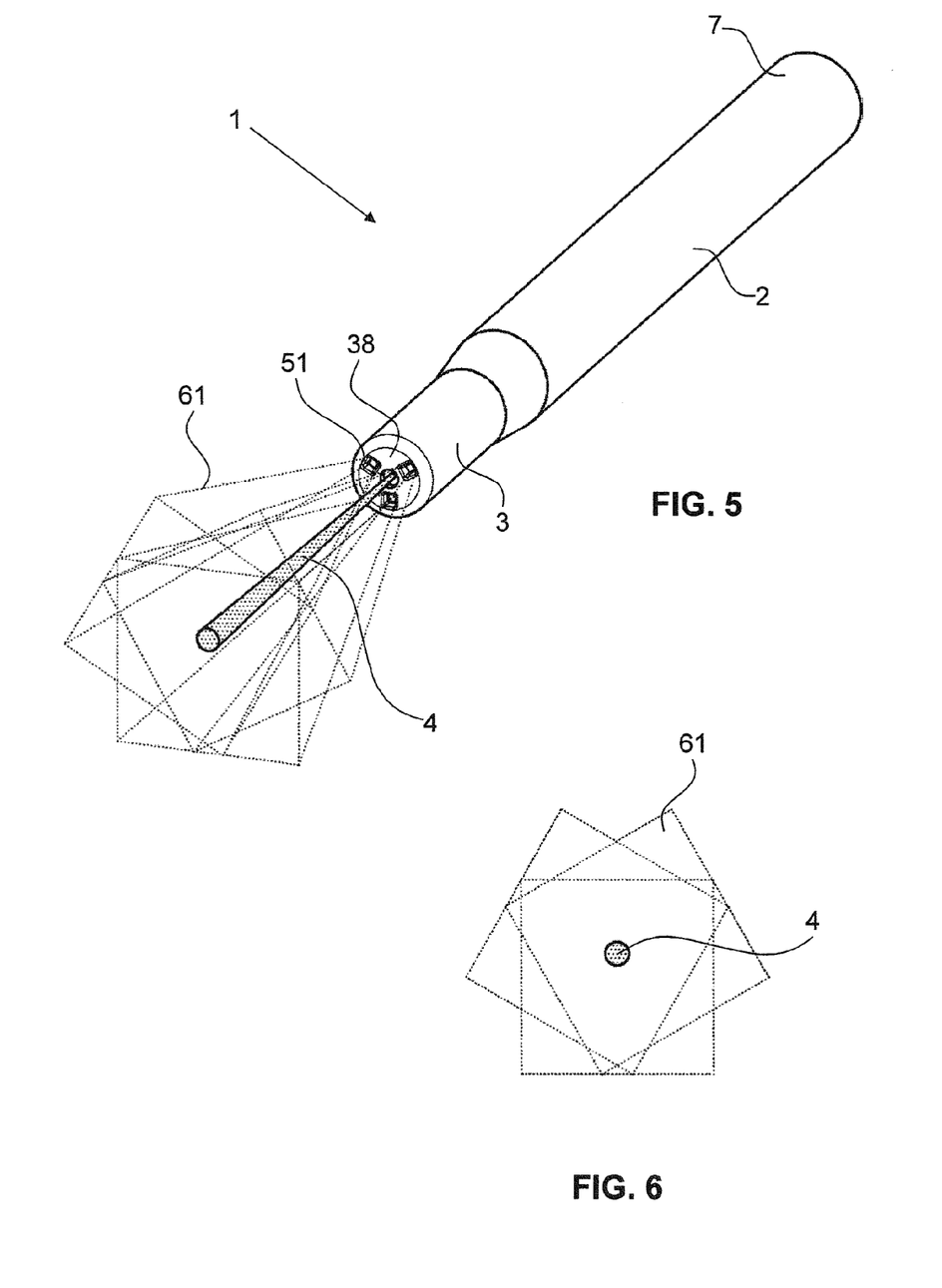
FIG. 5 shows a perspective illustration of a second embodiment of a system according to the invention for cleansing wounds with a fluid jet, with a light cone and fluid jet.
FIG. 6 shows an illustration of an area with a fluid jet illuminated by a handpiece in accordance with FIG. 5.
Figure 7:
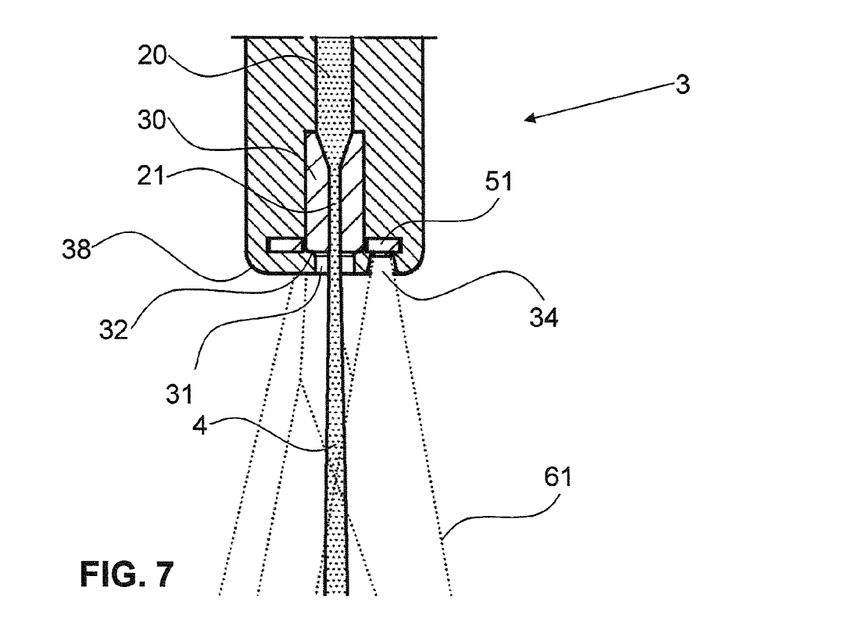
FIG. 7 shows a central sectional view of a front end of a handpiece in accordance with FIG. 5, with a light cone and fluid jet.
Figure 8:
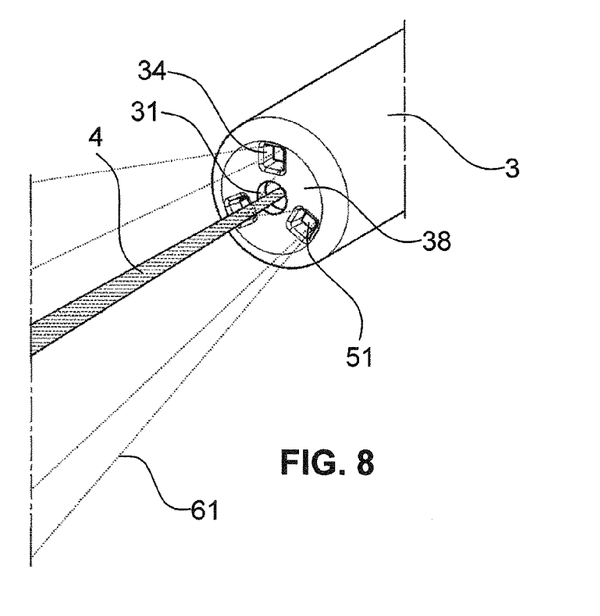
FIG. 8 shows a magnified perspective illustration of a front end of a handpiece in accordance with FIG. 5, with a light cone and fluid jet.

FIGS. 5, 7 and 8 show illustrations of a second embodiment of a system according to the invention for cleansing wounds with a fluid jet, with second light cones 61 and a fluid jet 4, wherein the system is a handpiece 1 in this embodiment. FIG. 6 shows an illustration of an area with the fluid jet 4 illuminated by the handpiece 1 in accordance with FIGS. 5, 7 and 8.

The second light sources 51 of the second embodiment are UV-C light-emitting diodes, which are arranged on a printed circuit board (PCB).

The second light sources 51 have a rectangular cross section and they are arranged in corresponding rectangular second recesses 34. In this example, the second light sources 51 are arranged recessed from the front end face 38.

FIG. 6 shows an illustration of an area with a fluid jet 4 illuminated by the handpiece 1 in accordance with the second embodiment. In contrast to the first embodiment, the second recesses 34 for receiving the second light sources 51 form light-emergence regions which have substantially quadractic embodiments. Therefore, the light cones 61 have a pyramid-like form. The area irradiated by a second light source 51 therefore has a substantially rectangular form. The second light cones 61 envelop the fluid jet 4 or the latter extends within the emitted light.

As depicted in FIG. 7, the second recesses 34 expand in the jet/beam direction. The recesses for receiving the second light sources 51 are embodied in such a way that the printed circuit boards are held in the edge regions thereof.

Like in the first embodiment, the handpiece 1 has recesses for the electric supply lines for the second light sources 51. The handpiece 1 likewise has a fluid line 8 and electric line 9 at the rear end 7 thereof, although these lines are not depicted here.

Figures 9, 10:
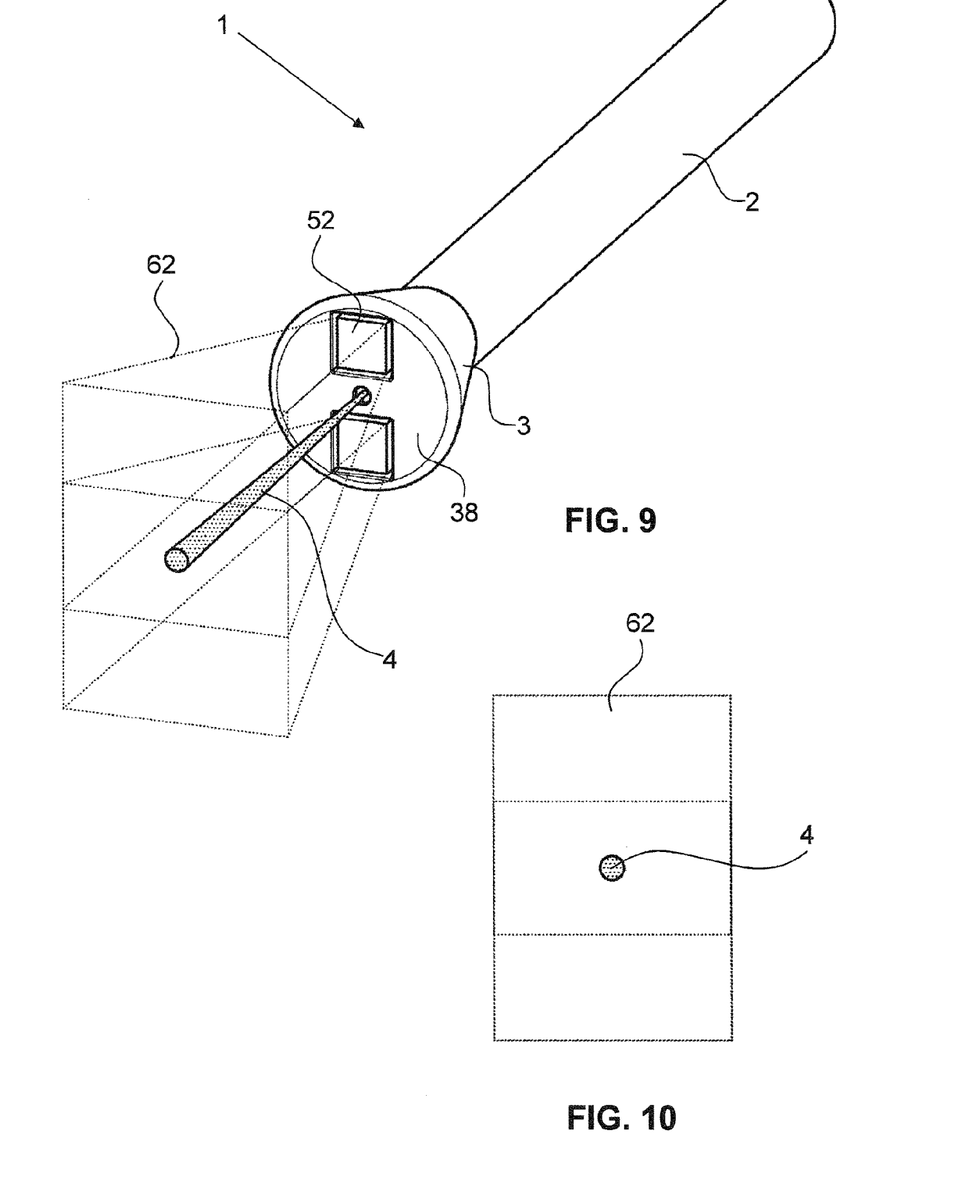
FIG. 9 shows a perspective illustration of a third embodiment of a system according to the invention for cleansing wounds with a fluid jet, with a light cone and fluid jet.
FIG. 10 shows an illustration of an area with a fluid jet illuminated by a handpiece in accordance with FIG. 9.
Figure 11:
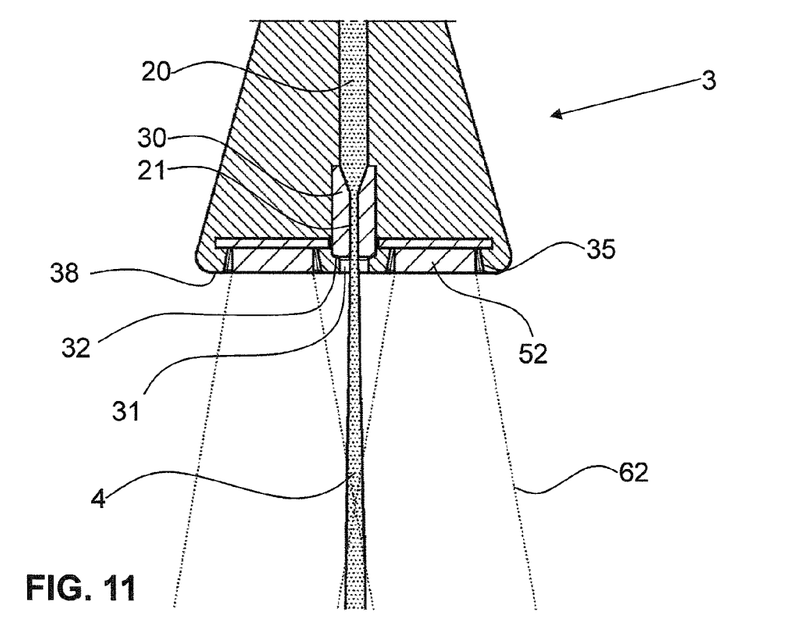
FIG. 11 shows a central sectional view of a front end of a handpiece in accordance with FIG. 9, with a light cone and fluid jet.
Figure 12:
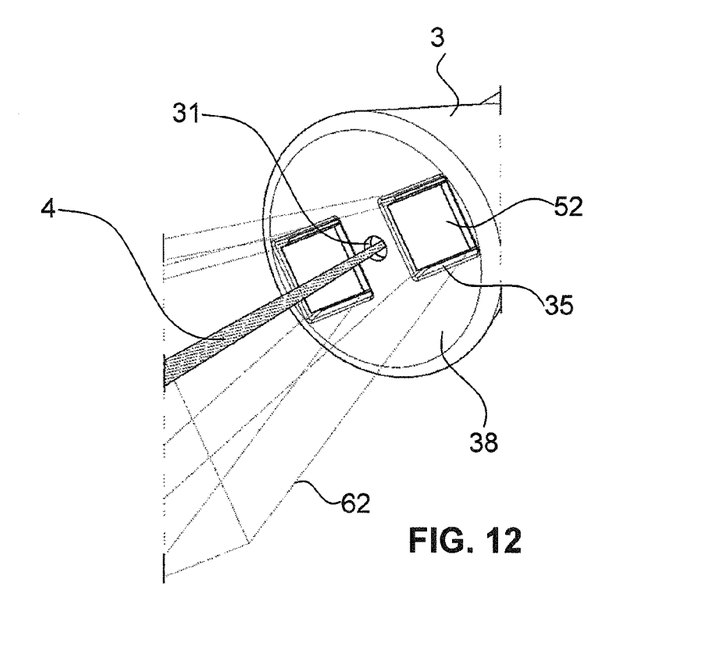
FIG. 12 shows a magnified perspective illustration of a front end of a handpiece in accordance with FIG. 9, with a light cone and fluid jet.

FIGS. 9, 11 and 12 show illustrations of a third embodiment of a system according to the invention for cleansing wounds with a fluid jet, with third light cones 62 and a fluid jet 4, wherein the system is a handpiece 1 in this embodiment. FIG. 10 shows a corresponding illumination image of the third embodiment.

The handpiece 1 in the third embodiment has a front end 3 expanded in the jet/beam direction for receiving two rectangular third light sources 52. As illustrated, the expansion can be uniform along the circumference; however, in a different exemplary embodiment, it can be embodied in such a way that the expansion is only present in the region of the light sources. The third light sources 52 are UV-C light-emitting diodes, which are integrated in an integrated circuit board (ICB).

The third light sources 52 have a rectangular cross section and they are arranged in corresponding rectangular third recesses 35. The third light sources 52 are arranged flush with the front end face 38.

FIG. 10 shows an illustration of an area with the fluid jet 4 illuminated by the handpiece 1 in accordance with the third embodiment. The third recesses 35 for receiving the third light sources 52 form light-emergence regions, which have a substantially rectangular embodiment. The third light cones 62 therefore have a pyramid-like form and the area irradiated by a third light source 52 therefore has a substantially rectangular form. The third light cones 62 envelop the fluid jet 4.

As depicted in FIG. 11, the third recesses 35 expand in the jet/beam direction. The recesses for receiving the third light sources 52 are embodied in such a way that they retain the printed circuit boards in the edge regions thereof.

Like in the first embodiment, the handpiece 1 has recesses for the electric supply lines for the third light sources 52. The handpiece 1 likewise has a fluid line 8 and electric line 9 at the rear end 7 thereof, although these lines are not depicted here.

Figures 13, 14:
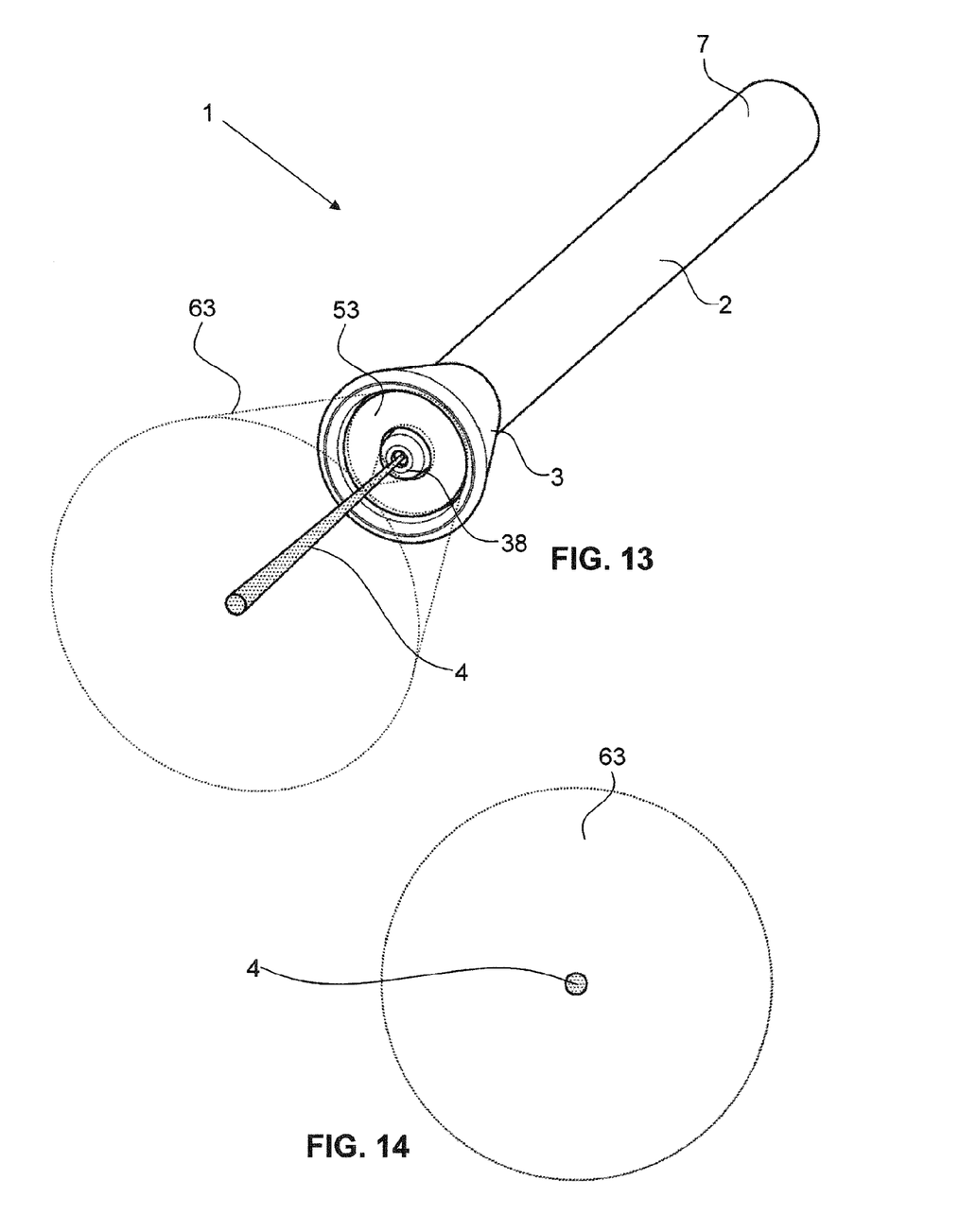
FIG. 13 shows a perspective illustration of a fourth embodiment of a system according to the invention for cleansing wounds with a fluid jet, with a light cone and fluid jet.
FIG. 14 shows an illustration of an area with a fluid jet illuminated by a handpiece in accordance with FIG. 13.
Figure 15:
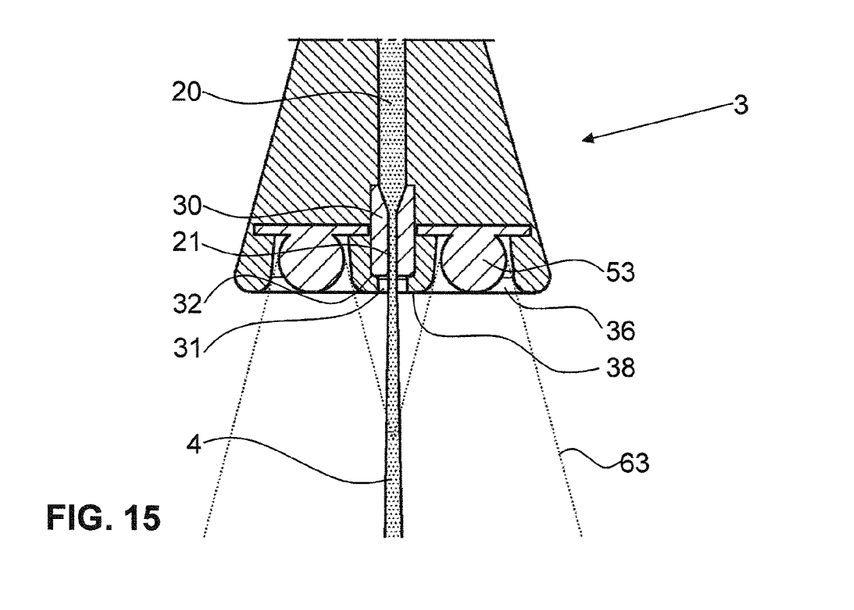
FIG. 15 shows a central sectional view of a front end of a handpiece in accordance with FIG. 13, with a light cone and fluid jet.
Figure 16:
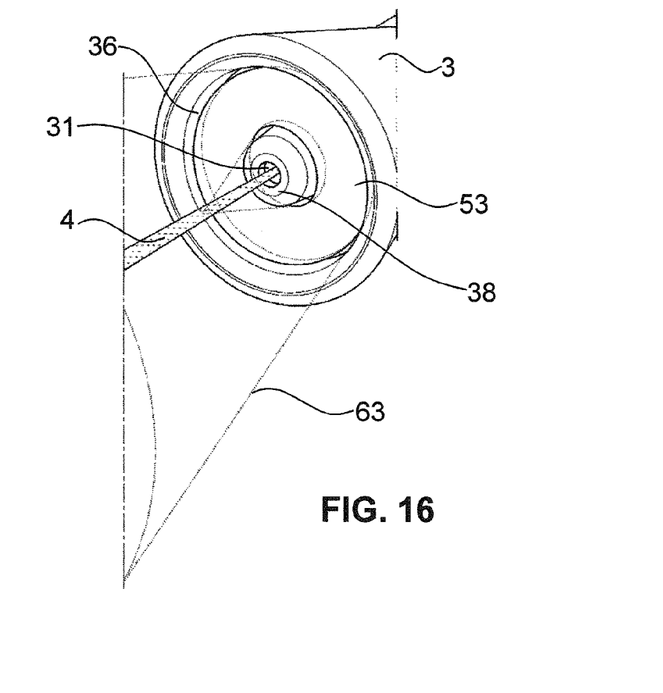
FIG. 16 shows a magnified perspective illustration of a front end of a handpiece in accordance with FIG. 13, with a light cone and fluid jet.

FIGS. 13, 15 and 16 show illustrations of a fourth embodiment of a system according to the invention for cleansing wounds with a fluid jet, with fourth light cones 63 and a fluid jet 4, wherein the system is a handpiece 1 in this embodiment. FIG. 14 shows a corresponding illumination image of the fourth embodiment.

The handpiece in the fourth embodiment has a front end 3 expanded in the jet/beam direction for receiving a toroidal fourth light source 53. The expansion is distributed uniformly at the circumference. The fourth light source 53 is a UV-C luminous element, which has a toroidal front part and a plate-shaped part adjoining at the rear side thereof. The plate-shaped part substantially has the form of a circular disk. By way of example, the fourth light source 53 is a UV-C mercury lamp or an LED.

The fourth light sources 53 are arranged in a corresponding fourth recess 36. The front end of the fourth light source 53 is arranged flush with the front end face 38.

FIG. 14 shows an illustration of an area with the fluid jet 4 illuminated by the handpiece 1 in accordance with the fourth embodiment. The fourth light cone 63 has a cone-like form and the area irradiated by a fourth light source 53 therefore has a substantially round form. The fourth light cone 6 envelops the fluid jet 4.

As depicted in FIG. 15, the fourth recesses 36 expand in the jet/beam direction. The recess for receiving the fourth light source 53 is embodied in such a way that it can retain the plate-shaped part thereof.

Like in the first embodiment, the handpiece 1 has recesses for the electric supply lines for the fourth light source 53. The handpiece 1 likewise has a fluid line 8 and electric line 9 at the rear end 7 thereof, although these lines are not depicted here.

Figure 17:
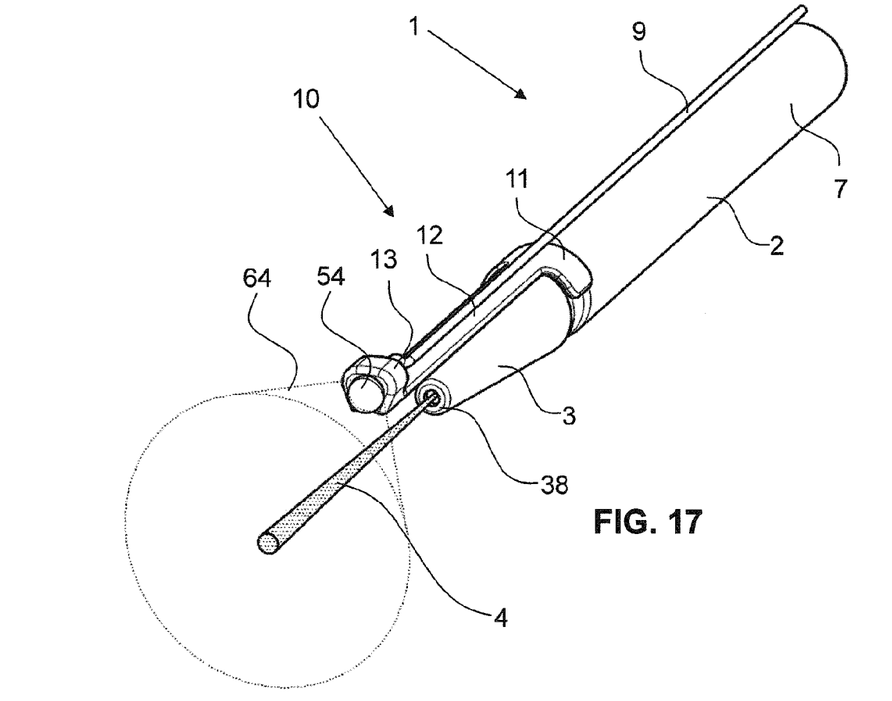
FIG. 17 shows a perspective illustration of a fifth embodiment of a system according to the invention for cleansing wounds with a fluid jet, with a light cone and fluid jet.
Figure 18:
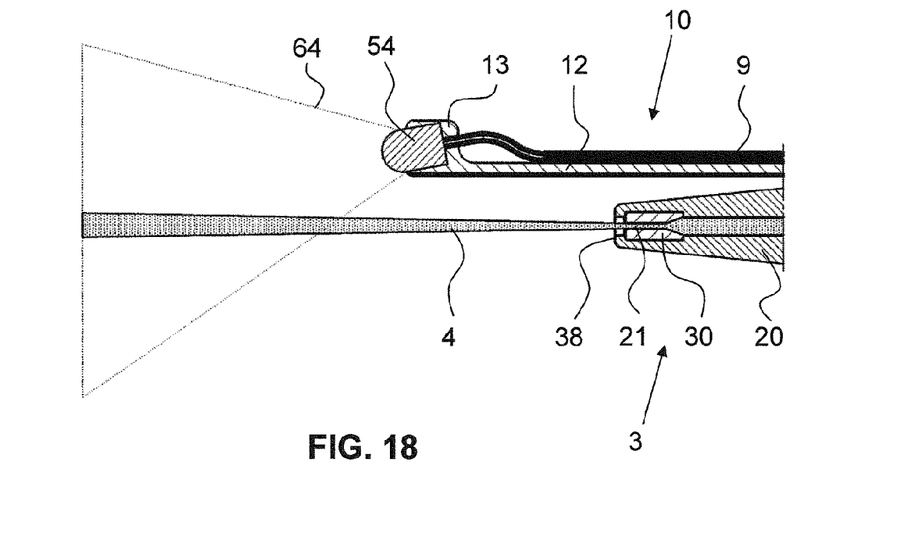
FIG. 18 shows a central sectional view of a front end of a handpiece in accordance with FIG. 17, with a light cone and fluid jet.

FIGS. 17 and 18 show illustrations of a fifth embodiment of a system according to the invention for cleansing wounds with a fluid jet, with a fifth light cone 64 and fluid jet 4.

The fifth embodiment has a handpiece 1 and a holder 10 arranged at this handpiece 1. In a clamping manner, the holder 10 is detachably connected with the handpiece 1 at the front end 3 thereof by way of clamping jaws 11. Provision is made for a side arm 12 adjoining the clamping jaws 11, which side arm, in the assembled state of the holder 10, extends substantially in the jet/beam direction. Provision is made for a light-source receptacle 13 adjoining the side arm 12 for receiving a fifth light source 54.

The fifth light source 54 preferably contains UV-C light-emitting diodes with round cross section. The diameter of the fifth light source 54 is many times larger than the diameter of the fluid jet 4. Preferably, it is at least five times larger, preferably at least 10 times larger.

As depicted in FIG. 18, the side arm 12 of the holder 10 projects beyond a front end face 38 of the handpiece 1. Therefore, the fifth light source 54 is arranged at a distance from the front end face 38 in the jet/beam direction. The fifth light cone 64 has a cone-like form and envelops the fluid jet 4.

At the rear end 7 thereof, the handpiece 1 has a fluid line 8, which is not depicted here. The fifth light source 54 is fed by an electric line 9, which connects the fifth light source 54 to an external current source.

The handpiece according to the invention enables wound cleansing with simultaneous decontamination of the aerosols created in the process such that the risk of contamination of the surroundings is reduced. Preferably, the wound is treated simultaneously with UV light.

What is claimed is:

1. A method for treating wounds with a fluid jet, the fluid jet having a diameter of 0.05 mm to 0.15 mm when emerging from an emergence opening and a pressure of 100 to 300 bar, the method using a system, wherein the system has at least one UV-C light source emitting light in the range of 200 to 280 nm, wherein the emitted UV-C light is used to irradiate and decontaminate aerosols created when cleansing a wound during a cleansing process by means of the fluid jet, the at least one UV-C light source having a toroidal front part that completely surrounds the fluid jet, and using the fluid jet, wherein in using the fluid jet, the emitted UV-C light forms a light cone completely enveloping the fluid jet and irradiates and decontaminates the aerosols located within the light cone and thereby reduces a risk of contamination of surroundings.

2. The method of claim 1 wherein the method is for cleaning wounds.

\* \* \* \* \*